United States Patent [19]

French

[11] 4,123,172

[45] Oct. 31, 1978

[54] COMPARISON TYPE COLORIMETER

[75] Inventor: Park French, Aurora, Ohio

[73] Assignee: Sterndent Corporation, Mount Vernon, N.Y.

[21] Appl. No.: 721,107

[22] Filed: Sep. 7, 1976

[51] Int. Cl.² .................................................... G01J 3/50
[52] U.S. Cl. ..................................... 356/188; 356/93; 356/212; 362/32
[58] Field of Search .................... 350/96 R, 96 B, 293; 356/39–41, 88, 89, 93–97, 104, 204, 205, 211, 212, 179, 180, 184, 186, 188, 189; 240/1 LP; 362/32

[56] References Cited

U.S. PATENT DOCUMENTS

| 2,892,378 | 6/1959 | Canada | 350/96 R X |
| 3,332,313 | 7/1967 | Batson | 356/179 |
| 3,461,856 | 8/1969 | Polanyi | 356/41 X |
| 3,926,501 | 12/1975 | Hama | 350/96 R X |
| 3,973,849 | 8/1976 | Jackson et al. | 356/95 X |
| 3,976,891 | 8/1976 | Parkinson | 356/207 X |

FOREIGN PATENT DOCUMENTS

| 1,212,743 | 3/1966 | Fed. Rep. of Germany | 356/205 |
| 661,425 | 11/1951 | United Kingdom | 356/205 |

Primary Examiner—F. L. Evans
Attorney, Agent, or Firm—Maky, Renner, Otto & Boisselle

[57] ABSTRACT

A comparison type colorimeter concentrates unknown and reference light beams onto the same surface area portion of a single photosensor and additionally filters the unknown and reference light beams by the same color filters and, preferably, portions thereof. Moreover, an enclosed light source produces light for the colorimeter to eliminate shift in illumination due to dust accumulation on the lamp and/or reflector of the light source.

18 Claims, 3 Drawing Figures

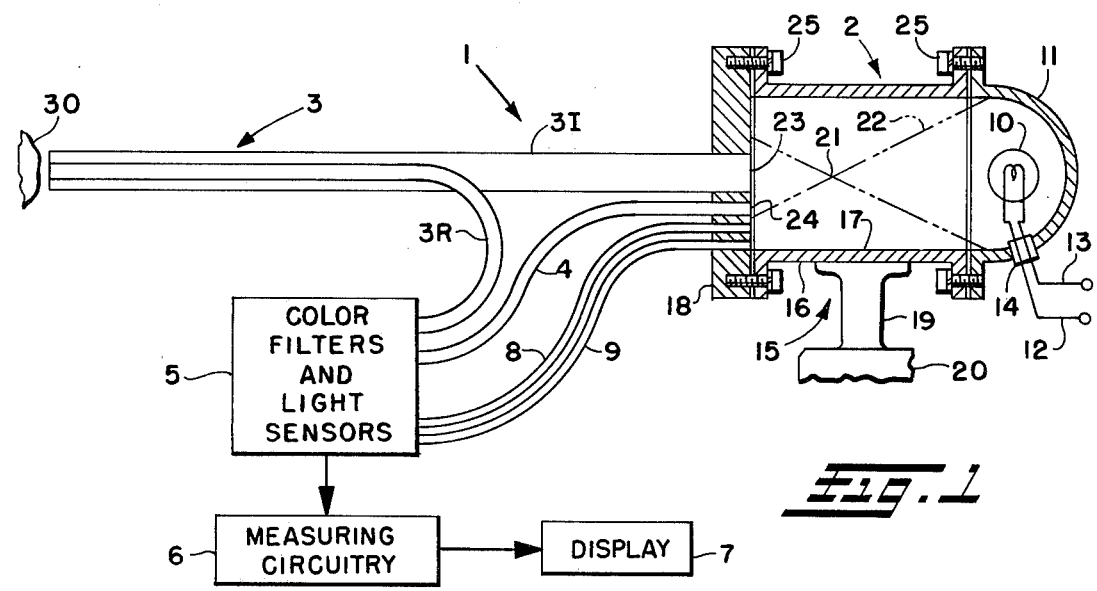
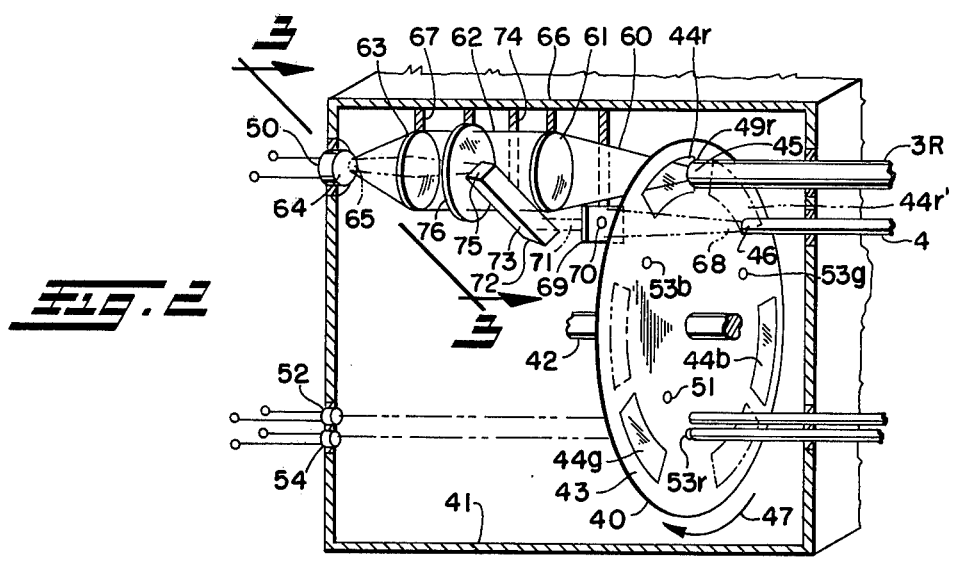
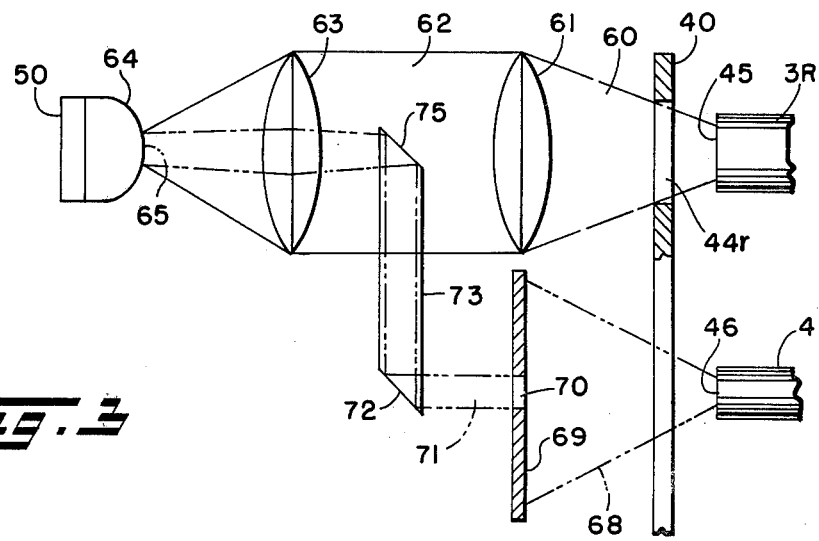

COMPARISON TYPE COLORIMETER

BACKGROUND OF THE INVENTION

The present invention relates generally, as indicated, to a comparison type colorimeter and, more particularly, to such a colorimeter that has improved accuracy in the optics portions thereof. Moreover, the present invention is directed to an enclosed stabilized light source to generate a uniform light output for use in such a comparison type colorimeter.

One source of error in photosensitive measuring instruments is encountered when light is directed onto different surface area portions of the photosensor, such as a photosensitive transistor, since equal intensities of light directed onto different surface area portions of a photosensor usually will produce different electrical outputs. Another source of error particularly in comparison type colorimeters has been encountered due to changes in the spectral properties of the color filters due to aging with the effects of such aging often being different for different respective filters and even for different respective portions of the same filter. Also, it has been found that the accumulation of dust on the lamp, reflector, and other elements of the light source of conventional colorimeters may cause a change or shift in the illumination output therefrom, thus causing still further error in the accuracy of the colorimeter.

SUMMARY OF THE INVENTION

In the present invention a light source includes an enclosure about a lamp to shield the same from dust and, thus, to enhance the stabilization of the light output therefrom, and light from that light source is directed via respective light pipes to illuminate an object to be optically measured or examined and to provide a reference light beam. Light from the object in an unknown light beam and the reference light beam are intermittently or sequentially directed onto the same surface area portion of the photosensor by providing both light beams as substantially parallel light to a single lens which focuses the parallel light inputs onto such common surface area portion. Further, the color filters of the colorimeter are mounted in a movable support, such as a color filter wheel, that sequentially and cyclically moves one portion of one color filter in the path of the unknown light beam and subsequently moves the same portion of that color filter to position in the light path of the reference light beam, thereby to assure that the color filtering effected of each light beam is the same.

The colorimeter accordingly effects a measurement of each color of the unknown light beam relative to each corresponding color of the reference light beam, whereby in a preferred embodiment the color values ultimately evolved and preferably displayed represent respective ratios of each color component of the unknown light beam to each corresponding color component of the reference light beam. Therefore, importantly, the colorimeter is substantially independent of the absolute intensity of the light source, which with aging may produce a light output of reduced absolute intensity but of substantially constant color temperature or spectral distribution. Similarly, the color and/or transmission characteristics of the several color filters may change with aging of the filters; however, the invention preferably assures that the unknown and reference light beams both pass through each color filter so that the mentioned ratios will remain substantially constant. Moreover, since the light source lamp and the incident light input ends of the respective light pipes exposed to the light source lamp preferably are shielded from dust and the like, the relative amounts of incident light received by the light pipes will remain substantially constant respective proportions of the light output from the light source lamp further to increase the accuracy of the colorimeter over relatively long periods of time.

Also, in the invention an infrared filtering arrangement is provided to filter both the unknown and reference light beams thereby to reduce substantially a previous source of error due to the transmission of infrared light through the color filters and the abnormal sensitivity of some solid state photosensors to infrared light or radiation. This infrared filtering also is conveniently effected in the detector portion of the colorimeter, as opposed to the light source portion, so that the infrared filter is maintained substantially at relatively constant ambient temperature and, therefore, does not change its transmission or filtering properties which are often temperature dependent.

It will be appreciated that although the preferred form of the invention described in the present application is directed to a comparison type colorimeter, the several features of the invention are also useful in other types of optical illuminating and measuring systems of both comparison and non-comparison types and of both colorimetric and non-colorimetric types.

With the foregoing in mind, a primary object of the invention is to improve the accuracy of response and measurement of a comparison type photosensor system or the like by directing a plurality of light beams onto the same surface area portion of the photosensor.

Another object is to reduce the disparity of a colorimeter caused by changes in color filters due to aging or the like.

An additional object is to increase the uniformity of filtering of plural light beams in a comparison type colorimeter or the like.

A further object is to stabilize the illumination output from a light source.

Still another object is to provide for adjustment in the light output of a light source and/or of the relative intensities of two light beams.

Still an additional object is to reduce or to eliminate errors due to infrared light in a colorimeter.

These and other objects and advantages of the present invention will become more apparent as the following description proceeds.

To the accomplishment of the foregoing and related ends, the invention, then, comprises the features hereinafter fully described, the following description and the annexed drawing setting forth in detail a certain illustrative embodiment of the invention, this being indicative, however, of but one of the various ways in which the principles of the invention may be employed.

BRIEF DESCRIPTION OF THE DRAWING

In the annexed drawing:

FIG. 1 is a broken away elevation view of an enclosed light source in accordance with the invention included in a comparison type colorimeter which is schematically shown;

FIG. 2 is a perspective view of the optics portion of a comparison type colorimeter in accordance with the invention; and FIG. 3 is a partial elevation view, partly in section, of the optics portion of the comparison type colorimeter of FIG. 2 looking generally in the direction of the arrows 3—3 thereof.

DESCRIPTION OF THE PREFERRED EMBODIMENT

Referring now more particularly to the drawing, wherein like reference numerals designate like parts in the several figures, a comparison type colorimeter in accordance with the invention is generally indicated at 1 in FIG. 1. The colorimeter includes a light source 2, a measuring light pipe 3, a reference light pipe 4, a color filters and light sensors portion 5, which is described in more detail below with reference to FIGS. 2 and 3, measuring circuitry 6, and a display portion 7. The colorimeter 1 also includes a pair of synchronizing light pipes 8, 9, which will also be described further below. The light pipes are preferably conventional flexible light conductive members of the solid or fiber type which are well known in the prior art.

The light source 2 includes a conventional lamp 10, such as an incandescent lamp, supported in conventional manner within the volume generally circumscribed by an ellipsoidal reflector 11. Leads 12, 13 of the lamp 10 extend through a conventional electrically non-conductive fitting 14 in the reflector 11 for connection to a source of preferably regulated electric power, not shown, to energize the lamp causing it to produce a light output. The reflector 11 is one part of the light source housing 15 that encloses the lamp 10 to shield the same from dust or other dirt accumulation thereon in order to assure that the illumination output therefrom will remain approximately constant for a constant electrical input thereto. The housing 15 further includes a cylinder or similar hollow connecting portion 16, which is fastened to the reflector 11 and preferably includes a blackened interior surface 17 to avoid light reflection thereby, and an end plate 18 in turn fastened to the cylinder 16. Each of the light pipes 3, 4, 8 and 9 has a light input end mounted in respective openings in the end plate 18 to receive light produced by the lamp in the housing 15, which is otherwise preferably light impermeable. The housing 15 is mounted by a pedestal 19 to support 20, such as the chassis of a colorimeter, whereby the light source 2 would be positioned within the colorimeter casing.

The ellipsoidal reflector 11 has an internal focus located within the volume circumscribed thereby and the lamp 10 is preferably positioned approximately at that focus. Therefore, the ellipsoidal reflector will tend to concentrate light produced by the lamp 10 at an external focus 21 of the ellipsoid, as is indicated by the light envelope 22 in FIG. 1. The external focus 21 is located within the cylinder 16 of the housing 15 such that the input ends 23, 24 of the light pipes 3 and 4 are within the spreading light area on the remote or far side of the focus 21 relative of the lamp 10 to receive a relatively concentrated light input from the light source 2. Fasteners 25 secure the reflector 11, cylinder 16 and end plate 18, and preferably light-tight seals are provided at the respective connections of the cylinder with the reflector and the end plate. It will be appreciated that by effecting relative translational movement of the various elements of the light source 2, the intensity of light received at the input ends 23, 24, may be increased or decreased, respectively, due to the inverse square law effect. Also, by moving the lamp 10 relative to the reflector 11 or the combined reflector and lamp, for example, in a vertical direction relative to the illustration in FIG. 1, the intensity ratios or proportions of light received by the light pipes 3, 4, respectively, may be varied. Moreover, although the synchronizing light pipes 8, 9 are normally positioned out of the area of concentrated light directed onto the end plate 18, the input ends of these light pipes receive sufficient light from the lamp 10 to energize respective photosensors in the color filters and light sensors portion 5 to provide synchronizing functions, as will be described further below.

The light pipe 3 has an incident light portion 3I that directs light received at the input end 23 from the light source 2 to an object 30 that is to be illuminated. The light pipe 3 also has a reflected light portion 3R that receives light reflected by the object 30 and directs the same to the color filters and light sensors portion 5 for comparison with light directed to the latter by the reference light pipe 4. In a preferred form of the invention the object 30 is a tooth and the colorimeter 1 is intended to measure the color of the tooth. However, it will be appreciated that the colorimeter 1 may be used to measure the color of objects other than teeth and, additionally, although the colorimeter is shown as a reflectance-type colorimeter, it may be modified in a conventional manner to measure light transmitted through an object.

From the foregoing it will be clear that the light source 2 and light pipes associated therewith provide a relatively closed light system for illuminating a sample and obtaining light therefrom and for generating a reference light beam that is compared by the color filters and light sensors 5 with the light from the object to determine the color or other optical properties of the latter. The light pipes 8 and 9 provide light inputs to the color filters and light sensors portion 5 for providing synchronizing signals, which indicate to the measuring circuitry 6 the color light being measured at any given time to synchronize the latter with the optics portion of the colorimeter 1. The display portion 7 provides a visual display in relative numerical form of the color values measured. However, if desired, the output electrical signals developed by the measuring circuitry may be provided to a recording apparatus, to a computer or other control system for controlling the color of the object 30, etc.

Turning now more particularly to FIG. 2, a color filter wheel 40 is positioned in a housing 41 of the color filters and light sensors portion 5 of the colorimeter mounted on a shaft 42 that is rotated by a motor, not shown. The wheel 40 includes a light impermeable supportive portion 43 within which are supported red, green and blue color filters 44r, 44g, 44b that are sequentially and cyclically positioned in alignment with respective output ends 45, 46 of the light pipes 3R and 4, respectively. The light pipe output ends 45, 46 are positioned at approximately the same radial distance from the center of the color filter wheel and are angularly spaced apart by approximately 40° so that as the color filter wheel 40 rotates substantially the same portion of each filter is placed in the respective paths of the light beams emanating from the output ends of those light pipes. The color filter wheel 41 rotates in a generally clockwise direction, as is indicated by the arrow 47 in FIG. 2, and the color filters are located thereon so that each of the color filters, such as the color filter 44r, will be sequentially and cyclically placed first in position to filter the unknown light from the light pipe 3R and, after the trailing edge 48r of the color filter 44r is rotated past the light pipe 3R to block light emanating therefrom and the leading edge 49r of the filter 44r is rotated past the light pipe 4, substantially the same portion of the color filter 44r will be placed then in the reference light beam emanating from that light pipe to filter the same. The thusly filtered unknown and reference light beams wil be sequentially supplied by the color filter wheel 40, which therefore acts as a chopper, to a measuring photosensor 50, such as a photosensitive transistor, as will be described further below.

The synchronizing light pipes 8, 9 have their output ends directly facing the color filter wheel 40 aligned on a common radial line of the color filter wheel but located at different respective distances from the center of the color filter wheel preferably closer to the center than are the color filters. An opening 51 in the color filter wheel 40 on each revolution of the color filter wheel briefly aligns with the light pipe 8 to pass light therefrom to a photosensor 52 which produces an electrical signal output directed to the measuring circuitry 6 to indicate to the latter that the next cyclical revolution of the color filter wheel is about to begin, thus synchronizing the measuring circuitry with the color filter wheel. Moreover, three additional openings 53r, 53g, 53b in the color filter wheel 40 are sequentially placed in alignment with the synchronizing light pipe 9 to pass light therefrom to a photosensor 54 that produces an electrical output to indicate to the measuring circuitry 6 that a respective color filter is then aligned in position with the output end of the light pipe 3R. One type of synchronizing and multiplexing circuit arrangement with which the colorimeter 1 and, particularly, the just-described synchronizing mechanism may be employed, is disclosed in U.S. Patent application Ser. No. 721,108 for "Improved Tristimulus Colorimeter", filed concurrently herewith, such application being assigned to the same assignee as the present application.

As is illustrated in FIG. 2 and in enlarged form in FIG. 3, the unknown light beam from the light pipe 3R emanates from the output end 45 of the latter generally within a conical envelope indicated at 60, and a lens 61 is positioned relative to the output end 45 to collimate or otherwise to concentrate that light beam as substantially collimated or parallel light indicated at 62. A further lens 63, which is preferably positioned slightly less than one focal length away from the light sensitive surface area 64 of the measuring photosensor 50, concentrates or focuses the collimated light 62 onto a particular portion 65 of the photosensor surface area. The lenses 61, 63 are preferably mounted in relatively fixed positions in the housing 41 by support members 66, 67, and the light pipe 3R and the photosensor 50 also are relatively fixedly mounted in the housing so that the surface area portion 65 on which light is concentrated will usually remain the same.

The reference light beam emanating from the light pipe 4 also is contained within a generally conical envelope 68, and in alignment with that envelope on the opposite side of the color filter wheel 40 from the light pipe 4 is an aperture plate 69 that blocks a portion of the reference light beam. The aperture plate has an opening 70 therein to pass a portion of the reference light substantially as parallel or collimated light 71 to the input end 72 of a prism reflector 73, which is mounted in the housing 41 by a support member 74. The length of the prism further helps to concentrate the passed portion of the reference light beam. The output end 75 of the prism reflector 73 is positioned between the two lenses 61, 63 so that the substantially parallel light provided the input end of the prism reflector is directed by the output end 75 to the lens 63, which will concentrate or focus that light onto the previously mentioned surface area portion 65 of the photosensor 50. It will be appreciated that the intensity of the reference light beam 71 passing the aperture plate 69 may be conveniently altered by effecting relative translational movement of the light output end 46 of the reference light pipe 4 due to inverse square law effects.

Preferably the cross-sectional area of the unknown collimated light beam portion 62 in its path between the two lenses 61, 63 is relatively large compared with the cross-sectional areas of the prism reflector 73 and the reference collimated light beam 72 directed in its path by the output end 75 of the prism toward the lens 63. Therefore, the effect of the prism reflector 73 in terms of attenuation of the unknown light beam will be minimal. Also, the prism reflector 73 may be substantially transparent so that an appreciable portion of the unknown light beam impinging thereon may pass therethrough.

A conventional infrared filter 76 is positioned in the housing 41 before the lens 63 to filter infrared light or radiation from both the unknown and reference light beams. The color filters 44r, 44g, 44b, which may be Kodak Wratten Gelatin Filters that have good color filtering properties, relatively readily transmit infrared light and the photosensor, which may be a solid state silicon type detector, and some other solid state detectors as well are extremely sensitive to infrared light. Therefore, in the present invention the infrared filter 76 blocks infrared light from the photosensor 50 and accordingly substantially eliminates errors due to infrared light. Additionally, by using the same infrared filter to filter both the unknown and reference light beams discrepancies caused by different filtering characteristics of plural filters, one in each light beam, are eliminated; and since the infrared filter is located away from the light source 2 and the heat produced by the latter, the optical transmission or filtering characteristics of that filter which ordinarily change with relatively large temperature changes are maintained substantially constant.

In FIG. 3, the color filter wheel 40 is shown in the same position as in FIG. 2 whereby the color filter 44r filters the unknown light emanating from the output end 46 of the light pipe 3R and passes the filtered unknown light to the lens 61, which collimates the light impinging thereon and directs that collimated light to the lens 63. The lens 63 focuses the light impinging thereon onto the surface area portion 65 of the photosensor 50. At a later time, however, after the color filter wheel 40 has rotated in a clockwise direction relative to the illustration of FIG. 2, the light impermeable supportive portion 43 of the color filter wheel blocks the unknown light and the filter 44r will have been rotated to the position shown in phantom at 44r′ in FIG. 2 so that the reference light beam 68 will be passed from the light pipe 4 via the color filter to the aperture plate 69. The light passed through the opening 70 in the aperture plate will be substantially collimated, as described above, and that substantially collimated light is directed by the prism reflector 73 to the lens 63, which focuses that light onto the same surface area portion 65 of the photosensor 50 as the unknown light was focused earlier.

The above-described operation of the invention, whereby the unknown light is filtered by one color filter and is detected by the photosensor 50 and thereafter the reference light is filtered by the same filter and, preferably, portion of the filter and is also detected by the same surface area portion of the photosensor, will occur sequentially for each color filter as the color filter wheel 40 rotates to place the respective color filters in alignment with the respective light pipes 3R and 4 and cyclically as long as the color filter wheel 40 continues rotating. The synchronizing electrical signals from the photosensors 52, 54 will synchronize the measuring circuitry 6 to the rotating color filter wheel 40 so that the measuring circuitry may operate, for example, as a multiplexed system to measure the electrical signals produced by the photosensor 50 which are representative of the intensity of light impinging thereon thereby to produce an output indicative of the ratios of the respective pairs of unknown and reference light beams. The output from the measuring circuitry will be provided to the display 7 for visually indicating the color of the object 30, for example, as values representative of respective ratios of each color component of the unknown light beam to the corresponding color components of the reference light beam.

It will, of course, be appreciated that although the preferred embodiment of the invention has been described above with reference to preferred focusing, reflecting, light transmitting and photosensitive elements, equivalent elements or combinations thereof may be substituted to perform correspondingly equivalent functions.

The embodiments of the invention in which an exclusive property or privilege is claimed are defined in the following claims:

1. A system for directing two different light beams onto substantially the same portion of the surface area of a photosensor, comprising:
   focusing means for focusing light onto a portion of the surface area of the photosensor, said focusing means comprising a lens positioned about one focal length from said photosensor,
   first collimating means for substantially collimating a first beam of light and directing the same to said focusing means,
   second means positioned in the path of at least part of said first beam for directing generally coaxially with said first beam, a second beam of light along a path in common with the path of said first beam of light to said focusing means, and
   chopper means for cyclically alternately passing light to said respective first and second means for directing,
   whereby said focusing means sequentially focuses each of said first and second beams of light onto substantially the same portion of the surface area of the photosensor,
   said first means for directing including means for supplying said first beam of light to said focusing means in a path having a relatively large cross-sectional area, and said second means for directing including means for directing said second beam of light to said focusing means as substantially collimated light having a relatively small cross-sectional area.

2. A system as set forth in claim 1, wherein said collimating means comprises a collimating lens and said second means is positioned between said lens and said collimating lens.

3. A system as set forth in claim 1, further comprising an infrared filter positioned between said focusing means and both of said first and second means to filter both of said light beams prior to impingement on the photosensor.

4. An illuminating apparatus for an optical measuring system, comprising means for generating light, housing means for substantially completely enclosing said means for generating light to shield the same from dust and the like, and light pipe means exposed to light in said housing means for directing such light exteriorly of said housing means to illuminate an external object, said housing means including reflector means for concentrating light from said means for generating light onto said light pipe means, said reflector means being generally of partial ellipsoidal shape, said means for generating light being positioned at least proximate the internal focus of such ellipsoid, and said light pipe means having a light input end positioned beyond the external focus of such ellipsoid relative to said means for generating light to receive generally diverging light.

5. An illuminating apparatus as set forth in claim 4, wherein said housing means includes end plate means for mounting said input end of said light pipe means to said housing means in alignment with said diverging light to be fully illuminated thereby.

6. An illuminating apparatus as set forth in claim 5, wherein the optical measuring system includes photosensitive measuring means for measuring light directed thereto from such external object, and the illuminating apparatus further comprises further light pipe means secured to said end plate means and exposed to light in said housing for directing a reference beam of light to said photosensitive measuring means.

7. An illuminating apparatus as set forth in claim 5, further comprising a second light pipe means, said second light pipe means having an input end also mounted by said end plate means in alignment beyond said external focus to be fully illuminated by said diverging light.

8. A system for directing two different light beams onto substantially the same portion of the surface area of a photosensor, comprising:
   focusing means for focusing light onto a portion of the surface area of the photosensor,
   first means for directing a first beam of light to said focusing means, and
   second means for directing a second beam of light to said focusing means,
   whereby said focusing means focuses both said first and second beams of light onto substantially the same portion of the surface area of the photosensor,
   said focusing means comprising a lens positioned approximately one focal length away from the photosensor,
   said first means comprising collimating means for substantially collimating said first beam of light, whereby said first beam of light directed to said lens is substantially collimated light,
   said second means having at least a portion positioned in the path of at least part of said first beam of light for directing said second beam of light along a path in common with the path of said first beam of light, said second means comprising further collimating means for substantially collimating said second beam of light, whereby said second beam of light directed to said lens is substantially collimated light, said further collimating means including aperture means for blocking a portion of said second beam of light with opening means for passing a portion of said second beam of light substantially as collimated light and elongate prism reflector means aligned with said opening means and said lens for directing said collimated light portion of said second beam of light to said lens, and wherein said collimating means comprises a collimating lens and at least a portion of said prism reflector means is positioned between said lens and said collimating lens.

9. A system for directing two different light beams onto substantially the same portion of the surface area of a photosensor, comprising:

focusing means for focusing light onto a portion of the surface area of the photosensor, first means for directing a first beam of light to said focusing means, and second means for directing a second beam of light to said focusing means, whereby said focusing means focuses both said first and second beams of light onto substantially the same portion of the surface area of the photosensor, said focusing means being positioned relative to the photosensor a distance such that said focusing means is operable to concentrate substantially collimated light supplied thereto onto the surface area portion of the photosensor, said first means for directing including means for supplying said first beam of light to said focusing means as substantially collimated light in a path having a relatively large cross-sectional area, and said second means for directing including means at least partly interposed in part of such path for directing said second beam of light to said focusing means as substantially collimated light having a relatively small cross-sectional area, and further comprising chopper means for cyclically and sequentially passing light to said first and second means for directing, said chopper means including color filter means for passing a predetermined color light and movable support means for moving said color filter means into position to pass such color light to only one of said first and second means for directing and subsequently into position to pass such color light to only the other of said first and second means for directing.

10. A system as set forth in claim 9, wherein said chopper means includes a plurality of color filter means for respectively passing different color light, and said movable support means includes means for cyclically and sequentially moving each of said color filter means to pass respective color light sequentially to said one and said other of said first and second means for directing.

11. A system as set forth in claim 10, further comprising an illuminating apparatus including means for generating light, housing means for substantially completely enclosing said means for generating light to shield the same from dust and the like, first light pipe means exposed to light in said housing means for directing such light exteriorly of said housing means to illuminate an external object thereby to produce said first beam of light and second light pipe means exposed to light in said housing means for directing such light exteriorly of said housing means to produce said second beam of light.

12. A system for directing two different light beams onto substantially the same portion of the surface area of a photosensor, comprising:

focusing means for focusing light onto a portion of the surface area of the photosensor, first means for directing a first beam of light to said focusing means, second means for directing a second beam of light to said focusing means, whereby said focusing means focuses both said first and second beams of light onto substantially the same portion of the surface area of the photosensor, and an illuminating apparatus including means for generating light, housing means for substantially completely enclosing said means for generating light to shield the same from dust and the like, first light pipe means exposed to light in said housing means for directing such light exteriorly of said housing means to illuminate an external object thereby to produce said first beam of light and second light pipe means exposed to light in said housing means for directing such light exteriorly of said housing means to produce said second beam of light.

13. A system as set forth in claim 12, wherein said housing means includes reflector means for concentrating light from said means for generating light onto said light pipe means, said reflector means being generally of partial ellipsoidal shape, said means for generating light being positioned at least proximate the internal focus of such ellipsoid, said housing means further including end plate means for mounting respective input ends of said first and second light pipe means to said housing means such that said input ends are positioned beyond the external focus of such ellipsoid relative to said means for generating light, and said housing means further including intermediate means between said reflector means and said end plate means for securing the same together, thereby to enclose said means for generating light.

14. A system as set forth in claim 13, further comprising means relatively remotely positioned with respect to said illuminating apparatus for filtering infrared light from both of said light beams prior to impingement of said light beams on the photosensor.

15. A system for directing two different light beams onto substantially the same portion of the surface area of a photosensor, comprising:

focusing means for focusing light onto a portion of the surface area of the photosensor, first means for directing a first beam of light to said focusing means, second means for directing generally coaxially with said first beam, a second beam of light to said focusing means, and chopper means for cyclically alternately passing light to said respective first and second means for directing, whereby said focusing means sequentially focuses each of said first and second beams of light onto substantially the same portion of the surface area of the photosensor, and said second means comprising aperture means for blocking a portion of said second beam and opening means for passing a portion of said second beam substantially as collimated light, and reflector means aligned with said opening means and said focusing means and including a portion generally in said first beam for directing said collimated light portion of said second beam, generally coaxially to said first beam, to said focusing means.

16. A system as set forth in claim 15, wherein said reflector means comprises an elongate prism having one surface for receiving at least part of said collimated light portion of said second beam, and another surface comprising said reflector means portion positioned generally in said first beam.

17. A system for directing two different light beams onto substantially the same portion of the surface area of a photosensor, comprising:
focusing means for focusing light onto a portion of the surface area of the photosensor,
first means for directing a first beam of light to said focusing means,
second means for directing a second beam of light to said focusing means,
chopper means for cyclically alternately and sequentially passing light to said respective first and second means for directing, said chopper means including color filter means for passing a predetermined color light and movable support means for alternately moving said color filter means into positions to pass light, third means aligned with said chopper means for directing one beam of light to and through only one portion of said color filter means when the latter is transmissively aligned therewith for delivery of such color light to only one of said first and second means for directing and fourth means aligned with said chopper means for directing another beam of light to and through the same portion of said color filter means as the latter is subsequently moved into transmissive alignment therewith for delivery of such color light to only the other of said first and second means for directing.

18. A system as set forth in claim 17, wherein said chopper means includes a plurality of color filter means for respectively passing different color light, and said movable support means includes means for cyclically and sequentially moving each of said color filter means to pass respective color light sequentially to said one and said other of said first and second means for directing.

* * * * *